United States Patent [19]

Porter

[11] Patent Number: 5,405,073
[45] Date of Patent: Apr. 11, 1995

[54] FLEXIBLE SUPPORT SHAFT ASSEMBLY
[75] Inventor: David S. Porter, Middlebury, Conn.
[73] Assignee: Ethicon, Inc., Somerville, N.J.
[21] Appl. No.: 162,557
[22] Filed: Dec. 6, 1993
[51] Int. Cl.[6] .......................................... A61B 17/068
[52] U.S. Cl. ....................................... 227/175; 227/19; 227/179
[58] Field of Search ............... 227/175, 176, 177, 178, 227/179, 19

[56] References Cited

U.S. PATENT DOCUMENTS

| | | | |
|---|---|---|---|
| 3,080,564 | 3/1963 | Strekopitov et al. | 1/50 |
| 3,275,211 | 9/1966 | Hirsch et al. | 227/124 |
| 3,315,863 | 4/1967 | O'Dea | 227/19 |
| 3,589,589 | 6/1971 | Akopov | 227/153 |
| 4,354,628 | 10/1982 | Green | 227/19 |
| 4,383,634 | 5/1983 | Green | 227/19 |
| 4,402,445 | 9/1983 | Green | 227/19 |
| 4,473,077 | 9/1984 | Noiles et al. | 128/305 |
| 4,508,253 | 4/1985 | Green | 227/19 |
| 4,527,724 | 7/1985 | Chow et al. | 227/8 |
| 4,566,620 | 1/1986 | Green et al. | 227/19 |
| 4,591,085 | 5/1986 | Di Giovanni | 227/8 |
| 4,610,383 | 9/1986 | Rothfuss et al. | 227/19 |
| 4,728,020 | 3/1988 | Green et al. | 227/19 |
| 4,869,414 | 9/1989 | Green et al. | 227/19 |
| 4,938,408 | 7/1990 | Bedi et al. | 227/8 |
| 4,941,623 | 7/1990 | Pruitt | 227/19 |
| 5,137,198 | 8/1992 | Nobis et al. | 227/19 |
| 5,139,513 | 8/1992 | Segato | 227/179 |
| 5,271,543 | 12/1993 | Grant et al. | 227/179 |

*Primary Examiner*—Scott A. Smith
*Attorney, Agent, or Firm*—Paul A. Coletti; Charles P. Boukus

[57] ABSTRACT

The present invention provides a flexible support shaft assembly which is capable of bending transversely relative to its longitudinal axis or centerline with a predetermined limit on the bending range. The flexible support shaft assembly comprises a first helical member with a series of coils of round cross section and a second helical member with a series of coils of wedge-shaped cross section. The first and second helical members are coiled together along a common longitudinal axis with the round coils alternating with the wedge-shaped coils which separate the adjacent round coils from each other when the support shaft assembly is straight. The wedge-shaped coils are slidable relative to the round coils to allow the support shaft assembly to bend into a curved shape until the round coils on the inside of the bend engage each other and limit the bending range.

24 Claims, 4 Drawing Sheets

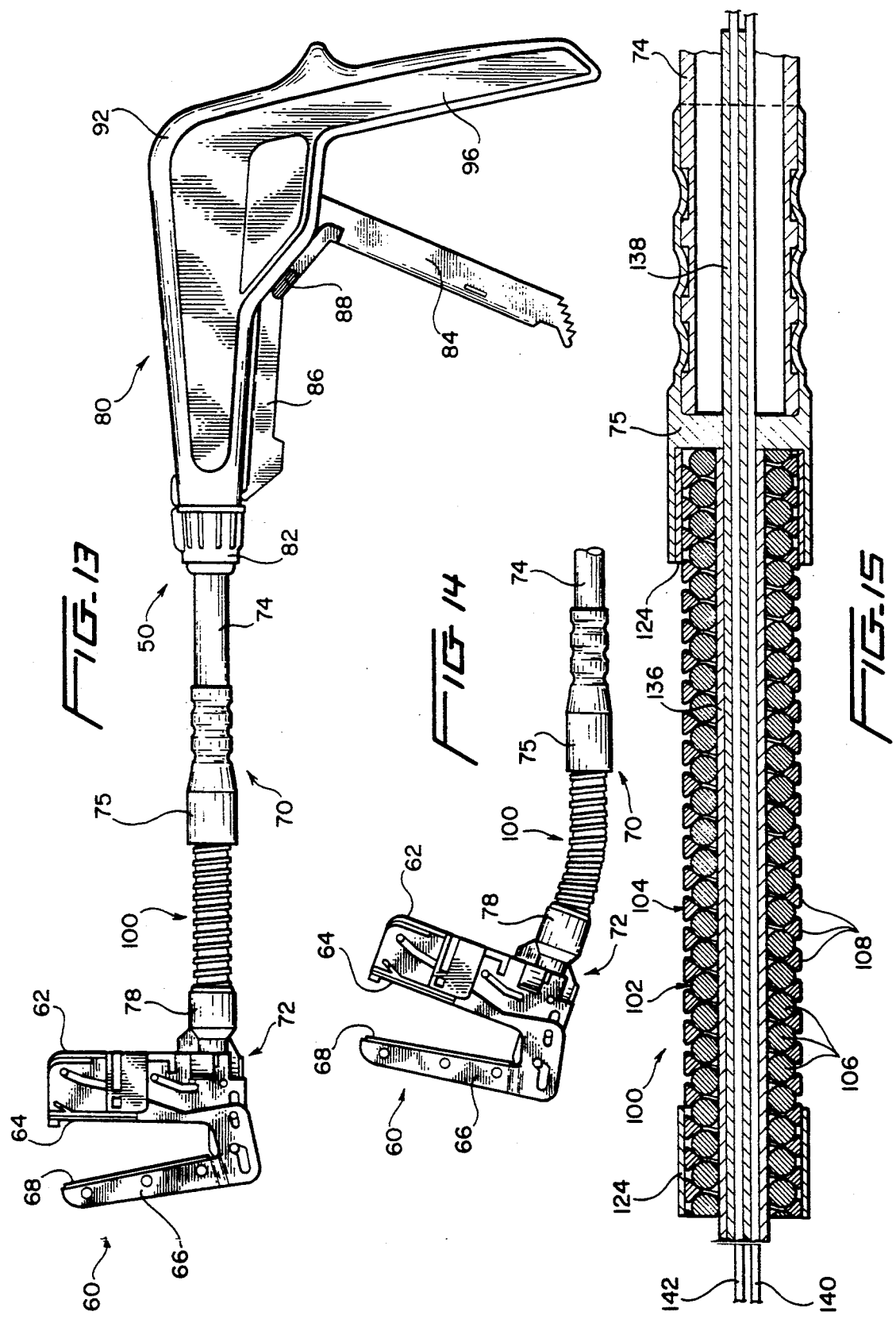

FLEXIBLE SUPPORT SHAFT ASSEMBLY

FIELD OF THE INVENTION

The present invention relates to a flexible support shaft assembly and, more particularly, to a flexible support shaft assembly comprising a pair of helical members which are coiled together and adapted to limit the bending range of the support shaft assembly.

BACKGROUND OF THE INVENTION AND PRIOR ART

In the prior art, it is known to provide a flexible tubular shaft for mounting a microphone. The flexible tubular support shaft can be flexed or bent into different curved shapes to allow the microphone to be adjusted to a desired position. Typically, an adjustable microphone support shaft comprises a pair of elongated helical elements each including a plurality of coils which are wound together along a common longitudinal axis. The coils engage each other with sufficient friction to allow the flexible support shaft to retain its bent shape and to hold the microphone in the desired position. Similarly, it is known to employ such flexible support shafts to mount adjustable lamps and fiberoptics devices.

In the case of flexible support shafts for microphones, it is desirable to provide a shaft construction which is capable of bending over a wide range of angles to facilitate the adjustment of the microphone into its desired position. No provision is made to impose a limit on the angle of bending of the flexible support shaft because of the advantages associated with a wide range of adjustment. Thus, the conventional microphone support shafts are not suitable for applications in which a limit on the bending range is required.

In co-pending U.S. patent application Ser. No. 832,299, filed on Feb. 7, 1992, entitled "Surgical Anastomosis Stapling Instrument With Flexible Support Shaft And Anvil Adjusting Mechanism", assigned to the same assignee as the present invention, a surgical stapling instrument including a flexible shaft assembly is disclosed. The flexible shaft assembly comprises a pair of elongated helical elements which are concentrically wound together with the coils of the first helical element alternately interspersed with the coils of the second helical element. Each coil of the first helical element has a round cross section and each coil of the second helical element has a triangular cross section provided with sloped surfaces which slidably engage the adjacent round coils. There is, however, no disclosure of any mechanism to limit the bending of the flexible shaft assembly.

Accordingly, it is an object of the present invention to provide a flexible support shaft assembly which is capable of bending transversely relative to its longitudinal axis or centerline with a predetermined limit on the bending range.

Another object of the invention is to provide a flexible support shaft assembly comprising a pair of helical members which are wound together along a common axis with the coils of the helical members interspersed and adapted to limit the transverse bending of the support shaft assembly.

It is also an object of the invention to provide a flexible tubular support shaft assembly comprising a dual coil structure in which a pair of helical members are coiled together and adapted to limit the bending range of the support shaft assembly for use in a device such as a surgical stapling instrument.

SUMMARY OF THE INVENTION

The present invention achieves a flexible support shaft assembly which is capable of bending transversely relative to its longitudinal axis or centerline with a predetermined limit on the bending range. The invention is embodied in a flexible support shaft assembly comprising a pair of helical members which are wound together along a common axis with the coils of the helical members interspersed with each other and adapted to limit the transverse bending of the support shaft assembly to a predetermined range. The flexible support shaft assembly is suitable for use in a surgical stapling instrument to limit the bending of the support shaft assembly to a predetermined range to avoid excessive frictional forces when the instrument is actuated by a surgeon.

The flexible support shaft assembly of the present invention comprises a first helical member including a series of coils of round cross section and a second helical member including a series of coils of wedge-shaped cross section. The first and second helical members are arranged with the round coils interspersed with the wedge-shaped coils which separate the adjacent round coils from each other when the support shaft assembly is straight. The wedge-shaped coils are slidable relative to the round coils to allow the support shaft assembly to bend in a transverse direction relative to its longitudinal axis until the round coils on the inside of the bend engage each other and limit the bending of the support shaft assembly.

In a preferred embodiment of the flexible support shaft assembly, the first helical member comprises a coil spring member and the second helical member comprises a wrap wire member which is wrapped about the coil spring member to position the wedge-shaped coils of the wrap wire member between the round coils of the coil spring member. The first and second helical members are coiled together along a common longitudinal axis with the round coils alternating with the wedge-shaped coils. The wedge-shaped coils separate the adjacent round coils from each other when the flexible support shaft assembly is straight to maintain the coil spring member in tension. The round coils and the wedge-shaped coils are secured together at the opposite ends of the support shaft assembly to maintain the tension in the coil spring member and prevent axial displacement of the coil spring member relative to the wrap wire member. The wedge-shaped coils are slidably engaged between the round coils and adapted to limit the support shaft assembly to a predetermined bending range. Preferably, each wedge-shaped coil is triangular in cross section and defines a set of inwardly sloped surfaces which slidably engage the adjacent round coils.

The sliding action of the wedge-shaped coils relative to the round coils allows the flexible support shaft assembly to bend into a curved configuration. The bending of the flexible support shaft assembly occurs without stretching the coil spring member along its axis until the round coils on the inside of the bend move into engagement with each other. Up to this point, the bending can be accomplished by applying a relatively small bending force to the flexible support shaft assembly. After the round coils on the inside of the bend engage each other, a substantially increased bending force is required to stretch the round coils on the outside of the bend to obtain any further bending of the support shaft assembly. Thus, the point at which the round coils on the inside of the bend move into engagement with each other defines a limit on the bending range of the support shaft assembly.

BRIEF DESCRIPTION OF THE DRAWINGS

The foregoing and other objects, aspects and advantages will be better understood from the following detailed description of the preferred embodiments of the invention with reference to the drawings, in which:

FIG. 13 is a side elevation of a surgical stapling instrument incorporating the flexible support shaft assembly of FIG. 7;

FIG. 14 shows the flexible support shaft assembly of FIG. 13 in a bent condition to adjust the orientation of the stapling head assembly; and FIG. 15 is an enlarged longitudinal section of the shaft assembly of the surgical instrument of FIG. 13.

DETAILED DESCRIPTION OF PREFERRED EMBODIMENTS

Figure 1:
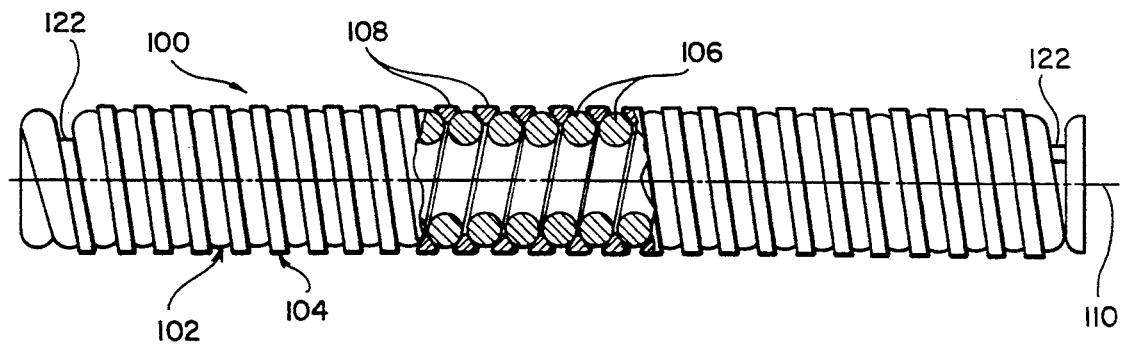
FIG. 1 is a partially cutaway side elevation of a flexible support shaft assembly constructed in accordance with this invention.
Figure 2:
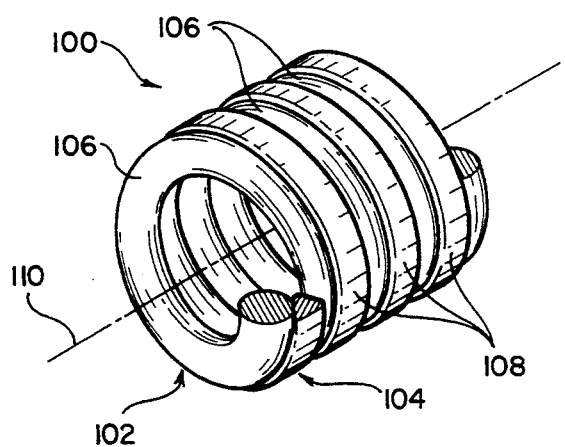
FIG. 2 is an enlarged, partially cutaway perspective view showing the dual coil structure of the flexible support shaft assembly of FIG. 1.
Figure 3:
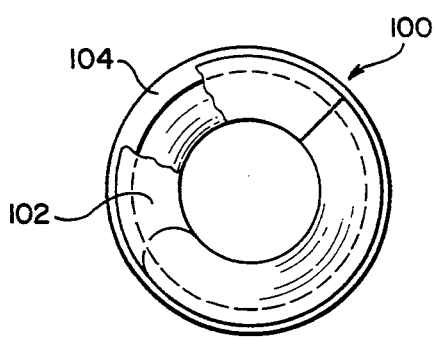
FIG. 3 is an end view showing the tubular shape of the support shaft assembly of FIG. 1.

Referring to FIGS. 1 and 2, the present invention is embodied in a flexible support shaft assembly 100 comprising a first elongated helical coil spring member 102 and a second elongated helical wrap wire member 104 concentrically wound together along a common longitudinal axis 110. The helical coil spring member 102 includes a series of coils 106 of round cross section. The helical wrap wire member 104 includes a series of coils 108 of wedge-shaped cross section. The coil spring member 102 and the wrap wire member 104 are arranged along the longitudinal axis 110 with the round coils 106 alternately interspersed with the wedge-shaped coils 108. Preferably, as shown in FIGS. 2 and 3, the flexible support shaft assembly 100 has a round tubular configuration.

Figure 4:
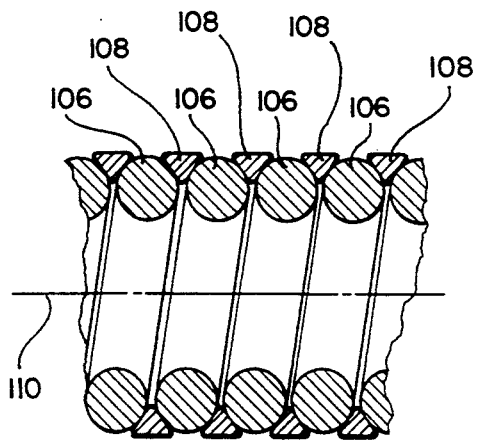
FIG. 4 is an enlarged longitudinal section showing a portion of the support shaft assembly of FIG. 1 in a straight condition.

As shown in FIG. 4, each of the wedge-shaped coils 108 initially separates the adjacent round coils 106 longitudinally from each other when the support shaft assembly 100 is straight. The round coils 106 and the wedge-shaped coils 108 are aligned along the common longitudinal axis 110. Preferably, each wedge-shaped coil 108 of the wrap wire member 104 has a triangular cross section defining a pair of inwardly sloped surfaces 112 (FIG. 6) which engage the round exterior surfaces 114 of the adjacent round coils 106. Each wedge-shaped coil 108 has a flat outer surface 116 which constitutes the base of the triangular cross section and a set of edges 118 which are rounded. The wedge-shaped coils 108 are slidable relative to the round coils 106 to allow the support shaft assembly 100 to bend in a transverse direction relative to its longitudinal axis 110. The sliding action of the wedge-shaped coils 108 allows the support shaft assembly 100 to bend until the round coils 106 (FIG. 5) on the inside of the bend engage each other and limit the bending of the support shaft assembly 100.

Figure 10:
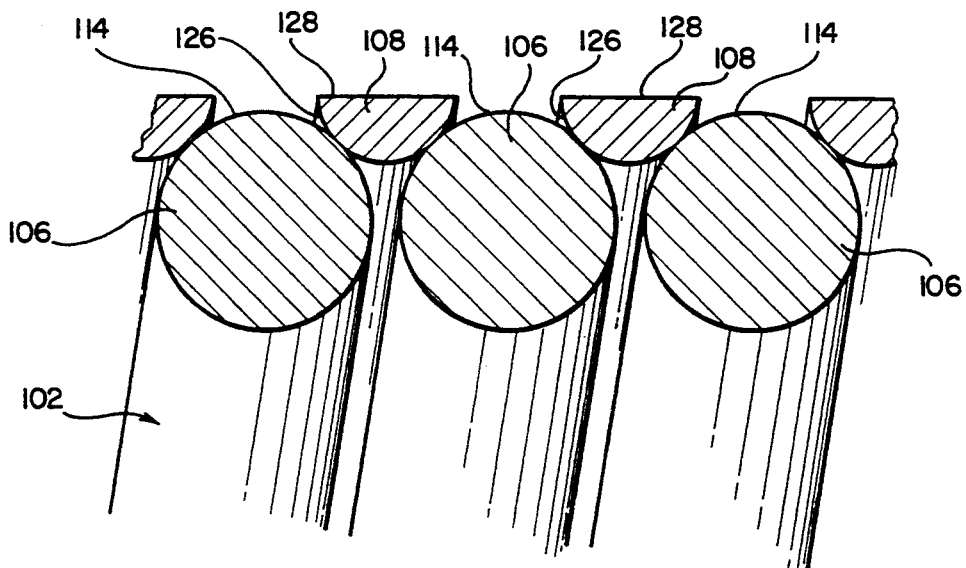
FIG. 10 is an enlarged fragmentary view of another embodiment of the support shaft assembly.

Alternatively, as shown in FIG. 10, the wedge-shaped coils 108 can be formed with a half-round cross section instead of a triangular cross section. Each of the half-round coils 108 includes an inner semi-circular surface 126 which engages the round exterior surfaces 114 of the adjacent round coils 106. In addition, each of the half-round coils 108 has a flat outer surface 128.

Figure 5:
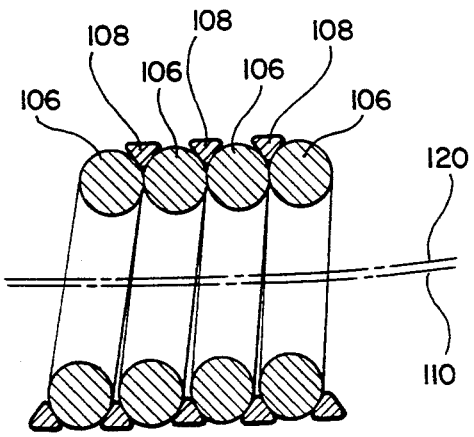
FIG. 5 is an enlarged longitudinal section showing a portion of the support shaft assembly of FIG. 1 in a bent condition.
Figure 6:
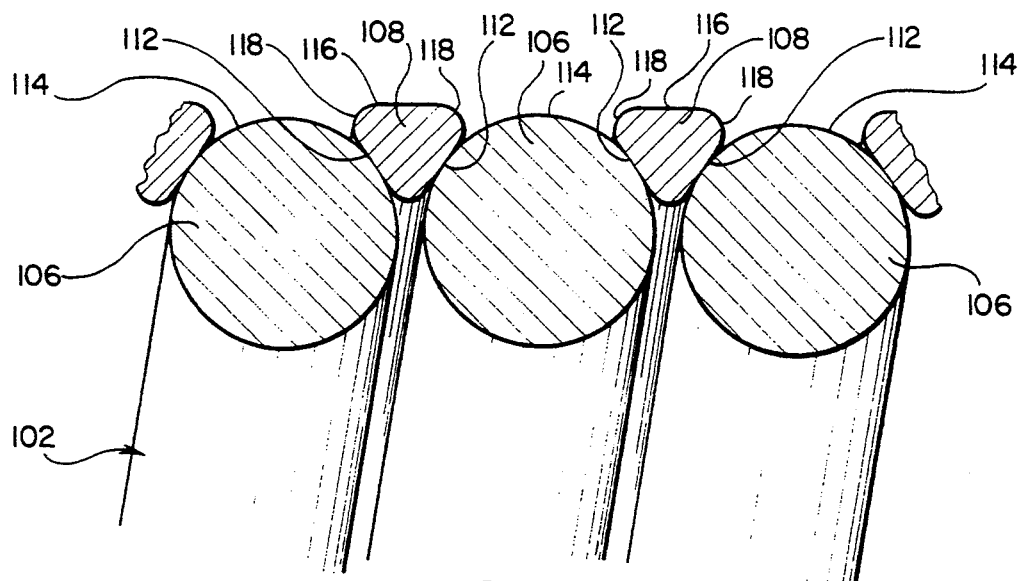
FIG. 6 is an enlarged fragmentary view of the coils of the support shaft assembly of FIG. 1.

Referring to FIG. 5, as the flexible support shaft assembly 100 is bent transversely relative to its longitudinal axis 110, the wedge-shaped coils 108 are shifted laterally relative to the adjacent round coils 106. Also, the longitudinal axis 120 of the wedge-shaped coils 108 is shifted slightly relative to the longitudinal axis 110 of the round coils 106 in the direction of the bending of the support shaft assembly 100. The portions of the round coils 106 on the inside of the bend move closer together while the portions of the round coils 106 on the outside of the bend move farther apart. As a result of the sliding action of the wedge-shaped coils 108 relative to the round coils 106, the flexible support shaft assembly 100 is bent into a curved configuration. The bending of the support shaft assembly 100 occurs without any substantial change in the overall length of the support shaft assembly 100 and without stretching of the coil spring member 102 along its axis 110 until the round coils 106 on the inside of the bend move into engagement with each other. Up to this point, the bending of the support shaft assembly 100 can be accomplished by applying a relatively small transverse bending force to the coil spring member 102 and the wrap wire member 104.

After the round coils 106 on the inside of the bend engage each other, a substantially increased bending force must be applied to obtain any further bending of the support shaft assembly 100 in the same direction. Because the portions of the round coils 106 on the inside of the bend are in contact with each other, any additional bending of the flexible support shaft assembly 100 requires the stretching of the coil spring member 102 to move the portions of the round coils 106 on the outside of the bend farther apart. Thus, the point at which the round coils 106 on the inside of the bend move into engagement with each other defines a limit on the bending of the support shaft assembly 100 in the transverse direction.

The desired limit on the bending range of the flexible support shaft assembly 100 is determined by the relative sizes and shapes of the round coils 106 of the coil spring member 102 and the wedge-shaped coils 108 of the wrap wire member 104. For example, to define a predetermined bending limit of about 30°, the ratio of the cross-sectional area of the round coils 106 to the cross-sectional area of the wedge-shaped coils 108 is about 6 to 1. Other predetermined bending limits can be provided by varying the ratio of the cross-sectional areas of the round coils 106 and the wedge-shaped coils 108.

In the dual coil structure of the flexible support shaft assembly 100 (FIG. 2), the helical coil spring member 102 and the helical wrap wire member 104 are coiled together with the coil spring member 102 in tension. The wrap wire member 104 is wrapped about the coil spring member 102 with the wedge-shaped coils 108 positioned between the round coils 106 to maintain a desired separation between the adjacent round coils 106 when the support shaft assembly 100 is straight. The wedge-shaped coils 108 are forced between the adjacent round coils 106 to maintain the coil spring member 102 in tension.

In addition, to maintain the tension in the coil spring 102 and prevent the axial displacement of the coil spring member 102 and the wrap wire member 104 relative to each other, the round coils 106 and the wedge-shaped coils 108 are secured together at the opposite ends of the support shaft assembly 100. For example, as shown in FIG. 1, at each end of the support shaft assembly 100, a portion 122 of the wrap wire member 104, i.e., the last half-turn of the last wedge-shaped coil 108, is bent radially inward and wedged between the last two round coils 106 of the coil spring member 102. The wedged portions 122 secure the ends of the coil spring member 102 and the wrap wire member 104 together and prevent any axial displacement of the coil spring member 102 and the wrap wire member 104 relative to each other when the flexible support shaft assembly 100 is bent. Alternatively, the round coils 106 and the wedge-shaped coils 108 at the opposite ends of the flexible shaft assembly 100 can be welded together, e.g., by one or more linear or spot welds, to secure the coil spring member 102 to the wrap wire member 104 at the opposite ends of the support shaft assembly 100.

In another embodiment of the flexible support shaft assembly 100 (FIG. 7), the coil spring member 102 and the wrap wire member 104 are secured together by a pair of clamping sleeves 124 at opposite ends of the support shaft assembly 100. Preferably, the clamping sleeves 124 are made of a compressible metal, e.g., aluminum, which can be compressed or swaged mechanically to clamp the wrap wire member 104 to the coil spring member 102.

Figure 7:
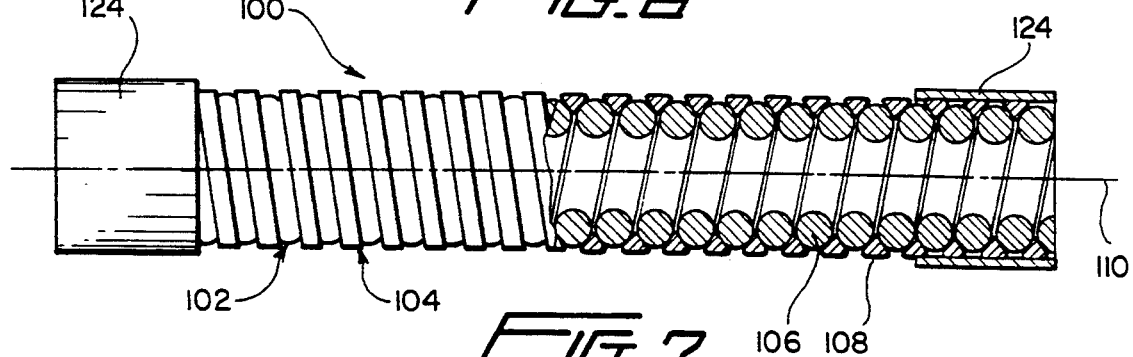
FIG. 7 is a partially cutaway side elevation showing an alternative embodiment of the flexible support shaft assembly.

Referring to FIG. 7, the dual coil structure of the flexible support shaft assembly 100 with the clamping sleeves 124 is assembled in the following manner. The wrap wire member 104 is wrapped about the coil spring member 102 to position the wedge-shaped coils 108 between the adjacent round coils 106 with the coil spring member 102 in tension. A series of clamping sleeves 124 made of compressible metal, e.g., aluminum, is positioned at uniformly spaced locations along the coiled helical members 102 and 104. Preferably, the clamping sleeves 124 are spaced apart by intervals of approximately three inches. Each of the clamping sleeves 124 is compressed or swaged mechanically to clamp the helical members 102 and 104 together. Then, the helical members 102 and 104 are divided into a plurality of flexible support shaft sections 100 of uniform length by cutting the helical members 102 and 104 at the mid-point of each clamping sleeve 124. Each of the resulting flexible tubular shaft sections 100 is clamped at its opposite ends by the clamping sleeves 124 to maintain the tension in the coil spring member 102 and prevent the unravelling of the coil spring member 102 and the wrap wire member 104.

In an example of the flexible support shaft assembly 100, the coil spring member 102 and the wrap wire member 104 are made of stainless steel wire. The coil spring member 102 consists of spring-tempered No. 302 stainless steel wire with a diameter of 0.120 inch. Each of the round coils 106 has an inner diameter of about 0.261 inch. The wrap wire member 104 consists of annealed No. 304 stainless steel wire formed with a triangular cross section. For example, the cross section of each wedge-shaped coil 108 is an isosceles triangle in which the width of the base is 0.055 inch and the apex angle is 70°. Each of the edges 118 (FIG. 6) of the wedge-shaped coils 108 is rounded at a radius of 0.007 inch. Each of the wedge-shaped coils 108 has an overall outside diameter of 0.52 inch. The support shaft assembly 100 has an overall length of 3.25 inches. The wedge-shaped coils 108 separate the adjacent round coils 106 from each other by approximately 0.006 inch when the support shaft assembly 100 is straight.

Figure 8:
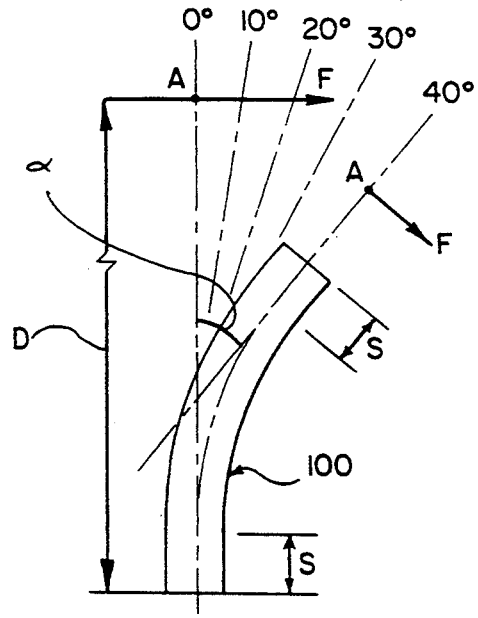
FIG. 8 is a diagram showing the deflection of the flexible support shaft assembly in response to a bending force.

Referring to FIG. 8, the deflection of the flexible support shaft assembly 100 can be tested as follows. Each end of the flexible support shaft assembly 100 has an unflexed longitudinal section S extending for a length of about 0.50 inch. One end of the flexible support shaft assembly 100 is fixed in place and a bending force F is applied via a rod (not shown) inserted into the opposite end of the support shaft assembly 100. The bending force F is applied at a point A located at a distance D of 6.75 inches from the fixed end of the support shaft assembly 100. The bending force F is applied at an angle of 90° to the centerline 110 at the free end of the support shaft assembly 100 for all bending angles in the deflection test.

Figure 9:
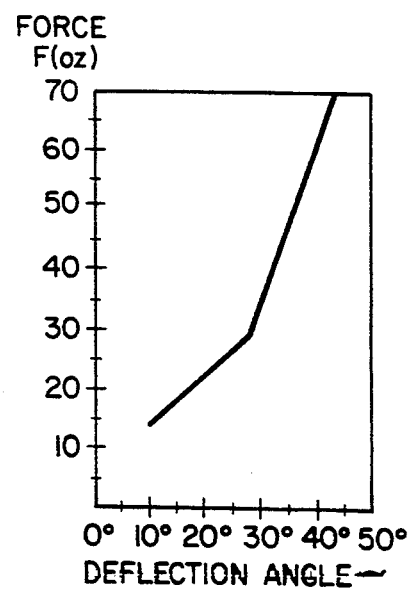
FIG. 9 is a graph illustrating the force-deflection characteristics of the flexible support shaft assembly.

FIG. 9 is a graph of the applied bending force F in ounces and the resultant angle α of deflection in degrees. As indicated in the graph, the flexible support shaft assembly 100 responds to the bending force F in a manner similar to a spring characterized by two different spring constants. At a deflection angle of approximately 30°, there is an abrupt increase in the force required to produce further bending of the support shaft assembly 100. For deflection angles less than 30°, the flexible support shaft assembly 100 exhibits a deflection-force characteristic of about 1½ degrees per ounce. For deflection angles greater than 30°, the support shaft assembly 100 exhibits a deflection-force characteristic of about 0.4 degrees per ounce. The abrupt change which occurs in the deflection-force characteristic at about 30° of deflection effectively provides a limit on the bending angle of the support shaft assembly 100.

Figure 11:
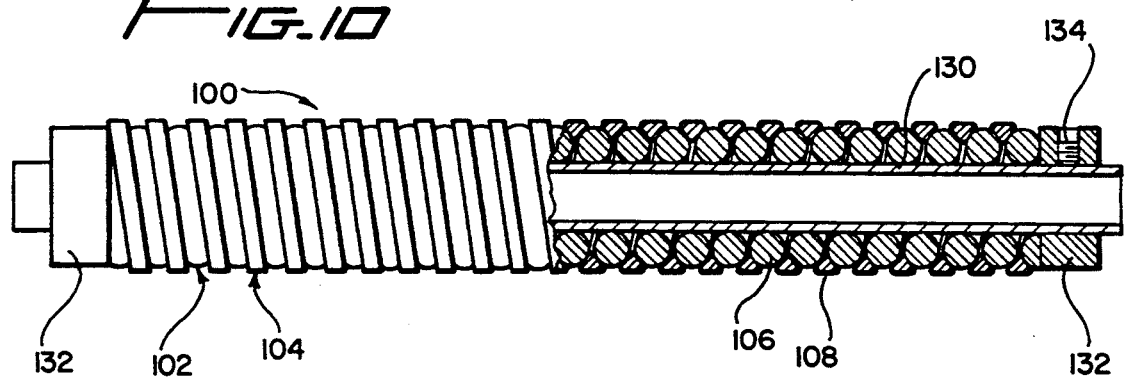
FIG. 11 is a partially cutaway side elevation showing a further embodiment of the flexible support shaft assembly.

In a further embodiment of the flexible support shaft assembly 100 (FIG. 11), the coil spring member 102 and the wrap wire member 104 are secured together by one or more linear or spot welds at the opposite ends of the coiled members 102 and 104. A flexible tubular member 130 extends axially through the coiled helical members 102 and 104. Preferably, the tubular member 130 consists of a malleable metal such as aluminum, which is capable of bending and maintaining the flexible support shaft assembly 100 in its bent or curved shape. A pair of collars 132 is mounted on the tubular member 130 adjacent to the opposite ends of the coiled helical members 102 and 104. Each of the collars 132 is secured, e.g., by one or more set screws 134 or by welding, at a fixed position on the tubular member 130. The collars 132 engage the opposite ends of the coiled helical members 102 and 104. The tubular member 130 and the collars 132 provide a stop mechanism which prevents the coil spring member 102 from stretching when the round coils 106 on the inside of the bend are engaged with each other to prevent the flexible support shaft assembly 100 from bending beyond a predetermined range.

Figure 12:
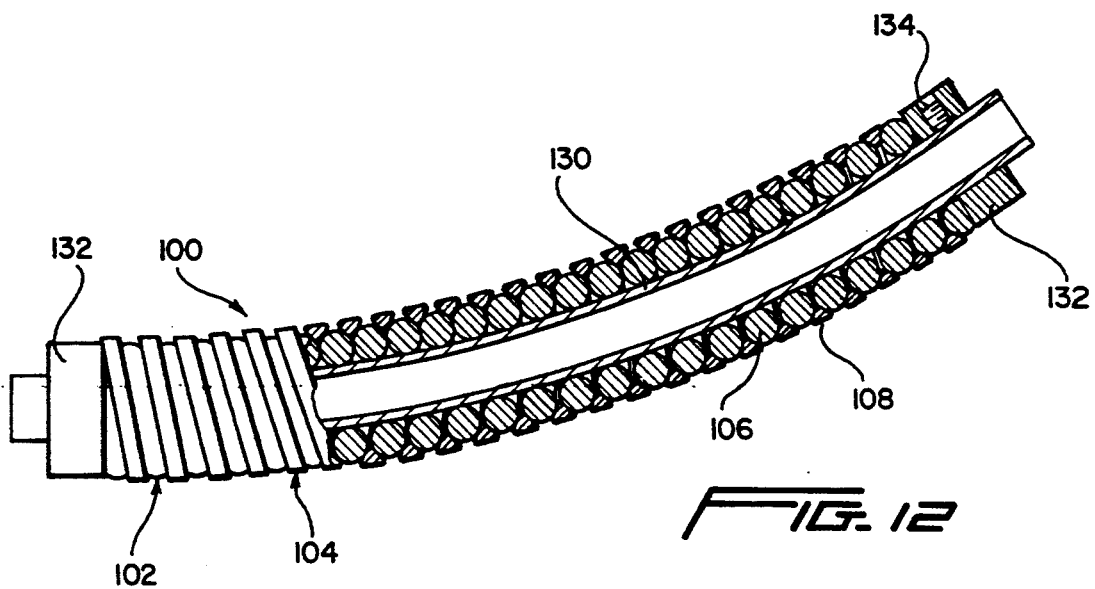
FIG. 12 shows the flexible support shaft assembly of FIG. 11 in a bent condition.

Referring to FIG. 12, when the flexible support shaft assembly 100 is bent in a transverse direction relative to its longitudinal axis 110, the wedge-shaped coils 108 slide relative to the round coils 106 to allow the flexible support shaft assembly 100 to assume a bent condition. The tubular member 130 is bent with the coiled helical members 102 and 104 into a curved shape. The portions of the round coils 106 on the inside of the bend move closer together while the portions of the round coils 106 on the outside of the bend move farther apart. The bending of the support shaft assembly 100 occurs without any substantial change in the overall length of the support shaft assembly 100 and without stretching the coil spring member 102 along its axis 110 until the round coils 106 on the inside of the bend move into engagement with each other. After the round coils 106 on the inside of the bend are engaged with each other, any further bending of the flexible support shaft assembly 100 requires the stretching of the coil spring member 102 to move the portions of the round coils 106 on the outside of the bend farther apart. However, the collars 132 which are secured at fixed positions to the tubular member 130 preclude any further stretching apart of the portions of the round coils 106 on the outside of the bend. The collars 132 function as stop members which preclude the bending of the flexible support shaft assembly 100 beyond the predetermined angle, e.g., 30°, at which the portions of the round coils 106 on the inside of the bend become engaged with each other.

Referring to FIG. 13, a surgical stapling instrument, generally 50, includes a distal stapling head assembly 60 connected by a support shaft assembly 70 to a proximal actuator handle assembly 80. The flexible support shaft assembly 100 of FIG. 7 is incorporated at the distal end of the shaft assembly 70. The flexible support shaft assembly 100 can bent in any radial direction relative to the longitudinal axis or centerline of the support shaft assembly 70 to facilitate the insertion of the stapling head assembly 60 at a desired surgical site within a human body and to enable the actuator handle assembly 80 to be located in a convenient orientation for actuation by a surgeon. The details of the stapling head assembly 60, shaft assembly 70, and actuator handle assembly 80 are described in a co-pending U.S. patent application entitled "Surgical Stapling Instrument With Articulated Stapling Head Assembly And Rotatable And Flexible Support Shaft", filed on the same date and assigned to the same assignee, Ethicon, Inc., as the present application, and herein incorporated by reference.

The stapling head assembly 60 includes a proximal or fixed jaw 62 which supports a staple cartridge 64 and a distal or movable jaw 66 which supports a staple forming anvil 68. The staple cartridge 64 receives one or more rows of staples (not shown) which are driven against the anvil 68 and formed into a B-shaped configuration to fasten tissue clamped between the jaws 62 and 66. The proximal or fixed jaw 62 is mounted in a hinge-like fashion on a pivot connection 72 which permits the stapling head assembly 60 to pivot about a vertical axis into different angular orientations relative to the support shaft assembly 70. In addition, the support shaft assembly 70 is rotatably mounted on the actuator handle assembly 80 for rotation about its longitudinal axis. A control knob 82 is rotatably mounted at the distal end of the actuator handle assembly 80 to allow the support shaft assembly 70 to be unlocked for rotation and to be locked in any desired rotational orientation.

The shaft assembly 70 includes a rigid tubular support shaft section 74 rotatably mounted on the actuator handle assembly 80 and secured by a coupling sleeve 75 to the flexible support shaft section 100. The hinge-like pivot connection 72 is mounted on a coupling sleeve 78 at the distal end of the flexible support shaft section 100. As shown in FIG. 14, the flexible support shaft section 100 is capable of bending in any radial direction relative to the longitudinal axis of the shaft assembly 70 into a bent or curved shape. The flexible support shaft section 100 limits the range of bending to approximately ±30° relative to the longitudinal axis of the shaft assembly 70.

The actuator handle assembly 80 includes a pivotally mounted closure lever 84 for closing the movable jaw 66 toward the fixed jaw 62 to clamp a tubular section of tissue between the jaws 62 and 66. The actuator handle assembly 80 also includes a pivotally mounted firing lever 86 for actuating the stapling head assembly 60 to drive the staples from the staple cartridge 64 through the tissue and to form the staples against the anvil 68. A firing safety lever 88 is pivotally mounted on the closure lever 84 to lock the staple firing trigger 86 and to prevent the firing of the staples in the staple cartridge 64 until the firing safety lever 88 is released. The actuator handle assembly 80 includes a pair of hollow handle sections 92 (one shown) which are adapted to snap fit together to support the jaw closure lever 84 and the staple firing trigger 86. Each of the handle sections 92 has a depending handle grip 96.

Referring to FIG. 15, inside the coil spring member 102 is a concentrically mounted cable support tube 136, preferably made of a malleable metal such as aluminum, which is capable of bending and maintaining the flexible support shaft section 100 in its bent or curved shape. The cable support tube 136 is flexible in any transverse direction relative to the longitudinal axis of the shaft assembly 70. A double lumen cable support member 138 is mounted inside the cable support tube 136 and provided with separate longitudinal passages for receiving a jaw closure cable 140 and a staple firing cable 142. The jaw closure cable 140 is actuated by the jaw closure lever 84 to close the movable jaw 66 and clamp the tissue between the stable cartridge 64 and the anvil 68. The staple firing cable 142 is actuated by the staple firing trigger 86, after the movable jaw 66 is closed, to actuate a staple driver mechanism (not shown) inside the fixed jaw 62 to staple the tissue together. When the flexible tubular shaft section 100 is bent into a curved shape to adjust the orientation of the stapling head assembly 60, the bending angle is limited to a maximum of 30° to avoid excessive frictional forces on the closure cable 140 and the firing cable 142 to insure that the jaw closure lever 84 and the staple firing trigger 86 can be actuated by the surgeon.

The invention in its broader aspects is not limited to the specific details of the preferred embodiments shown and described, and those skilled in the art will recognize that the invention can be practiced with modification within the spirit and scope of the appended claims.

I claim:

1. A flexible support shaft assembly, comprising:
   a first helical member including a series of coils of round cross section transverse to the longitudinal axis of said coils;
   a second helical member including a series of coils of wedge-shaped cross section transverse to the longitudinal axis of said coils;
   said first and second helical members being arranged with said round coils interspersed with said wedge-shaped coils which separate the adjacent round coils from each other when said support shaft assembly is straight; and
   said wedge-shaped coils being slidable relative to said round coils to allow said support shaft assembly to bend in a transverse direction relative to its longitudinal axis until the round coils on the inside of the bend engage each other and limit the bending of said support shaft assembly.

2. The support shaft assembly of claim 1, wherein:
   said first and second helical members are coiled together with said first helical member in tension.

3. The support shaft assembly of claim 2, wherein:
   said wedge-shaped coils are slidably engaged between said round coils and adapted to limit said support shaft assembly to a predetermined bending range.

4. The support shaft assembly of claim 3, wherein:
   each of said wedge-shaped coils is triangular in cross section.

5. The support shaft assembly of claim 3, wherein:
   each of said wedge-shaped coils defines a set of inwardly sloped surfaces which slidably engage the adjacent round coils.

6. The support shaft assembly of claim 1, wherein:
   the ratio of the cross sectional areas of said round coils and said wedge-shaped coils is about 6 to 1.

7. The support shaft assembly of claim 1, which includes:
   stop means for preventing said first helical member from stretching when the round coils on the inside of the bend engage each other to preclude the bending of said support shaft assembly beyond a predetermined range.

8. The support shaft assembly of claim 7, wherein said stop means includes:
   a flexible tubular member extending axially through said first and second helical members;
   a pair of stop members mounted on said tubular member adjacent to the opposite ends of said first and second helical members; and
   said stop members engaging said helical members to prevent the round coils on the outside of the bend from stretching apart when the round coils on the inside of the bend are engaged with each other.

9. A flexible support shaft assembly, comprising:
   a helical coil spring member including a series of coils of round cross section transverse to the longitudinal axis of said coils;
   a helical wrap wire member including a series of coils of wedge-shaped cross section transverse to the longitudinal axis of said coils;
   said helical coil spring member and said helical wrap wire member being arranged along a common longitudinal axis with said round coils alternating with said wedge-shaped coils which separate the adjacent round coils longitudinally from each other when said support shaft assembly is straight; and
   said wedge-shaped coils being slidable relative to said round coils to allow said support shaft assembly to bend in a transverse direction relative to its longitudinal axis until the round coils on the inside of the bend engage each other and limit the bending of said support shaft assembly.

10. The support shaft assembly of claim 9, wherein:
    said wrap wire member is wrapped about said coil spring member to position said wedge-shaped coils between said round coils with said coil spring member in tension.

11. The support shaft assembly of claim 9, wherein;
    said wedge-shaped coils are slidably engaged between said round coils and adapted to limit said support shaft assembly to a predetermined bending range.

12. The support shaft assembly of claim 11, wherein:
    each of said wedge-shaped coils is triangular in cross section.

13. The support shaft assembly of claim 11, wherein:
    each of said wedge-shaped coils defines a set of inwardly sloped surfaces which slidably engage the adjacent round coils.

14. The support shaft assembly of claim 9, wherein:
    the ratio of the cross sectional areas of said round coils and said wedge-shaped coils is about 6 to 1.

15. The support shaft assembly of claim 9, which includes:
    stop means for preventing said coil spring member from stretching when the round coils on the inside of the bend engage each other to preclude the bending of said support shaft assembly beyond a predetermined range.

16. The support shaft assembly of claim 15, wherein said stop means includes:
    a flexible tubular member extending axially through said coil spring and wrap wire members;
    a pair of stop members mounted on said tubular member adjacent to the opposite ends of said coil spring and wrap wire members; and
    said stop members engaging said helical members to prevent the round coils on the outside of the bend from stretching apart when the round coils on the inside of the bend are engaged with each other.

17. In a surgical stapling instrument including a stapling head assembly for stapling tissue together, an actuator handle assembly for actuating said stapling head assembly, and a flexible support shaft assembly for connecting said stapling head assembly to said actuator handle assembly to permit the orientation of said stapling head assembly to be adjusted relative to said actuator handle assembly by bending said flexible support shaft assembly, said flexible support shaft assembly comprising:
    a first helical member including a series of coils of round cross section transverse to the longitudinal axis of said coils;
    a second helical member including a series of coils of wedge-shaped cross section transverse to the longitudinal axis of said coils;
    said first and second helical members being arranged with said round coils interspersed with said wedge-shaped coils which separate the adjacent round coils from each other when said support shaft assembly is straight; and said wedge-shaped coils being slidable relative to said round coils to allow said support shaft assembly to bend in a transverse direction relative to its longitudinal axis until the round coils on the inside of the bend engage each other and limit the bending of said support shaft assembly.

18. The support shaft assembly of claim 17, wherein:
said first and second helical members are coiled together with said first helical member in tension.

19. The support shaft assembly of claim 18 wherein:
said wedge-shaped coils are slidably engaged between said round coils and adapted to limit said support shaft assembly to a predetermined bending range.

20. The support shaft assembly of claim 19, wherein:
each of said wedge-shaped coils is triangular in cross section.

21. The support shaft assembly of claim 19, wherein:
each of said wedge-shaped coils defines a set of inwardly sloped surfaces which slidably engage the adjacent round coils.

22. The support shaft assembly of claim 17, wherein:
the ratio of the cross sectional areas of said round coils and said wedge-shaped coils is about 6 to 1.

23. The support shaft assembly of claim 17, which includes:
stop means for preventing said first helical member from stretching when the round coils on the inside of the bend engage each other to preclude the bending of said support shaft assembly beyond a predetermined range.

24. The support shaft assembly of claim 23, wherein said stop means includes:
a flexible tubular member extending axially through said first and second helical members;
a pair of stop members mounted on said tubular member adjacent to the opposite ends of said first and second helical members; and
said stop members engaging said helical members to prevent the round coils on the outside of the bend from stretching apart when the round coils on the inside of the bend are engaged with each other.

* * * * *